Figure 1:
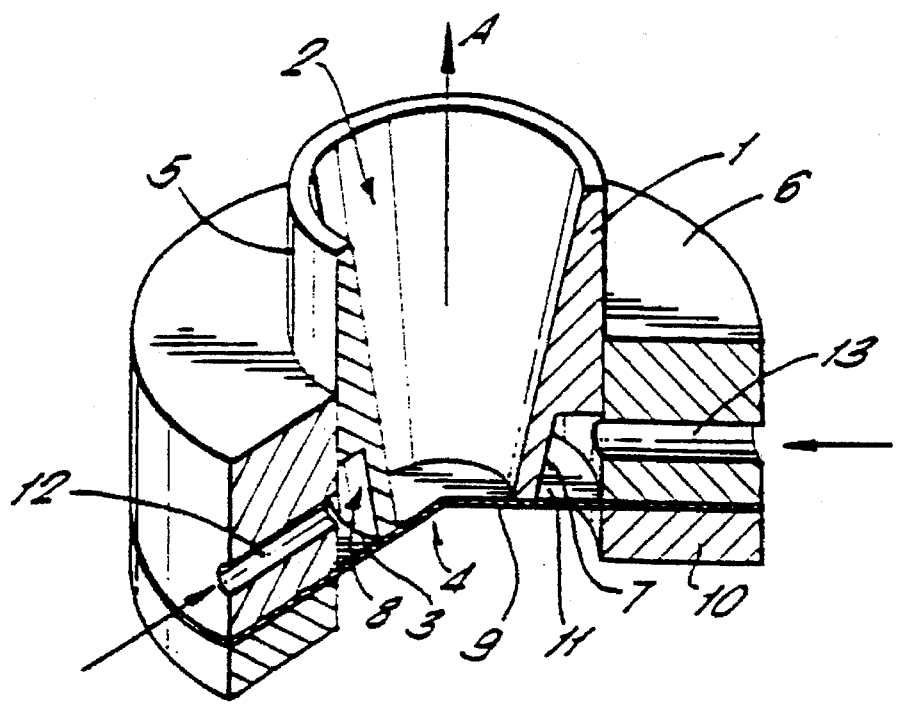

United States Patent
Barnes et al.

[11] Patent Number: 5,653,227
[45] Date of Patent: Aug. 5, 1997

[54] ATOMIZING DISPENSER

[75] Inventors: Paul Barnes, King's Lynn; Andrew Robert Fry, Barnet; John David Marsh, Royston, all of United Kingdom

[73] Assignee: Bespak PLC, Norfolk, United Kingdom

[21] Appl. No.: 571,831

[22] PCT Filed: Jun. 23, 1994

[86] PCT No.: PCT/GB94/01357

§ 371 Date: Dec. 26, 1995

§ 102(e) Date: Dec. 26, 1995

[87] PCT Pub. No.: WO95/00254

PCT Pub. Date: Jan. 5, 1995

[30] Foreign Application Priority Data

Jun. 23, 1993 [GB] United Kingdom ............... 9312984

[51] Int. Cl.$^6$ ............................................. A61M 11/02
[52] U.S. Cl. ........................ 128/203.12; 128/200.16; 128/203.15
[58] Field of Search .................. 128/203.12, 203.15, 128/203.21, 203.24, 203.23, 200.16; 604/58; 222/636; 141/50; 239/102.1, 251, 255

[56] References Cited

U.S. PATENT DOCUMENTS 3,473,530  10/1969  Urbanowicz .
5,113,855  5/1992  Newhouse .

FOREIGN PATENT DOCUMENTS 2450801  5/1976  Germany .
826176   5/1981  U.S.S.R. .
922310   3/1963  United Kingdom .

OTHER PUBLICATIONS

*Database WPI*, 24 Mar. 1982, Derwent Publications Ltd., London, GB: AN B4027.

*Primary Examiner*—Vincent Millin
*Assistant Examiner*—Robert N. Wieland
*Attorney, Agent, or Firm*—Beveridge, DeGrandi, Weilacher & Young L.L.P.

[57] ABSTRACT

A gas supply (30) supplies pressurized gas to a nozzle (1) such that a flow of gas is discharged through an aperture (77) defined between a lip (3) of the nozzle and a vibrating diaphragm (9). A liquid dispenser (42) introduces a metered quantity of liquid into the gas flow such that the liquid droplets are atomized by the vibrating diaphragm. The diaphragm is held under tension so that it is vibrated by the gas flow. The supply of gas may be a manually operated displacement or diaphragm pump or may be a pressurized gas container. Metered doses may be dispensed for oral inhalation without providing external energy source for the vibration of the diaphragm.

34 Claims, 8 Drawing Sheets

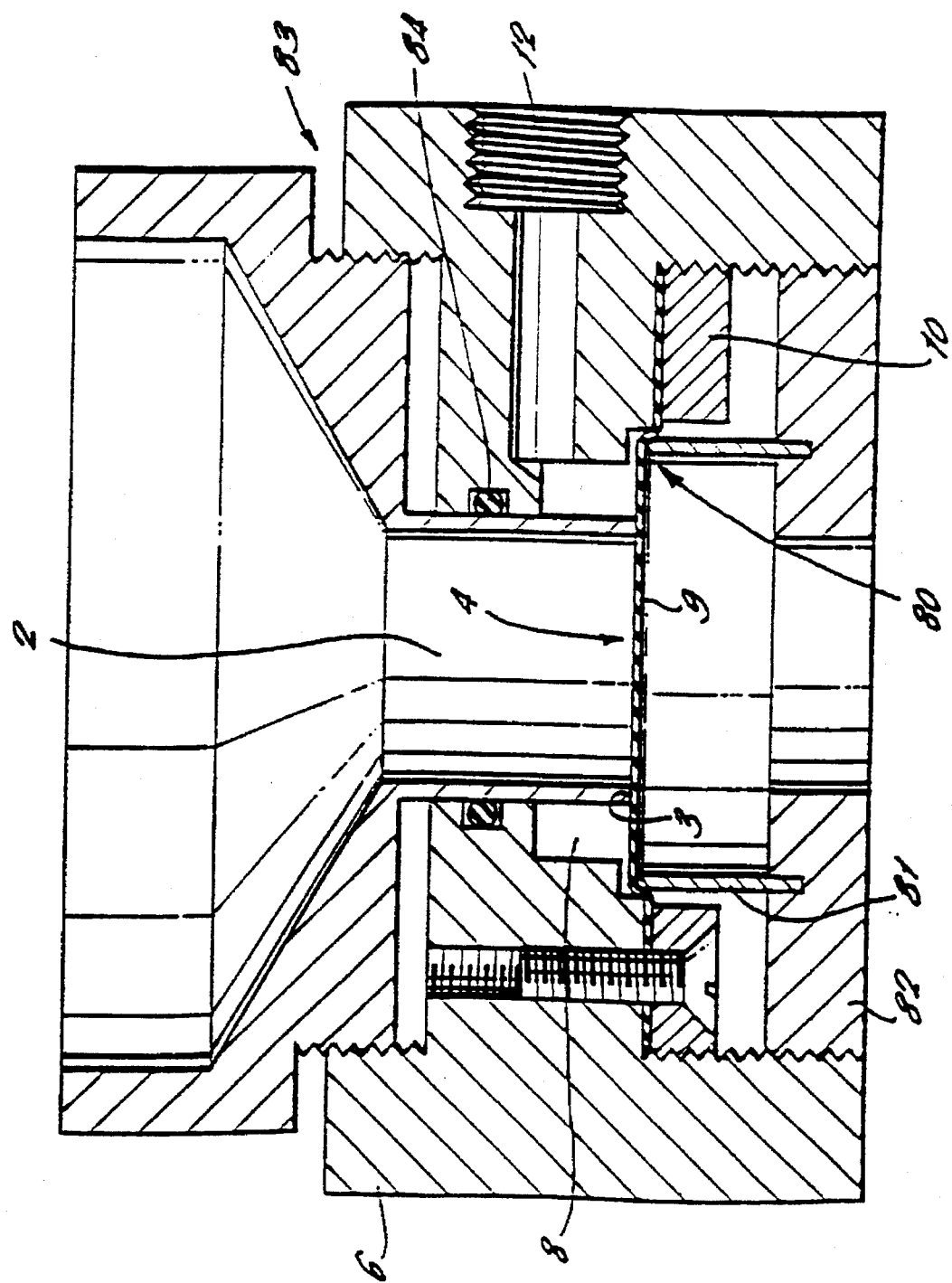

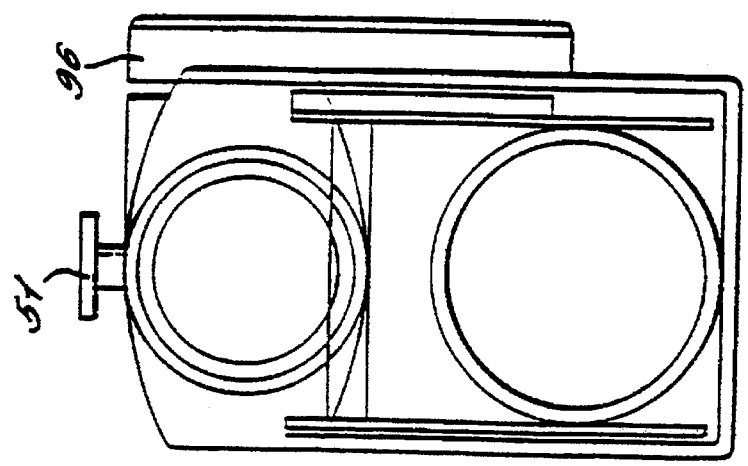
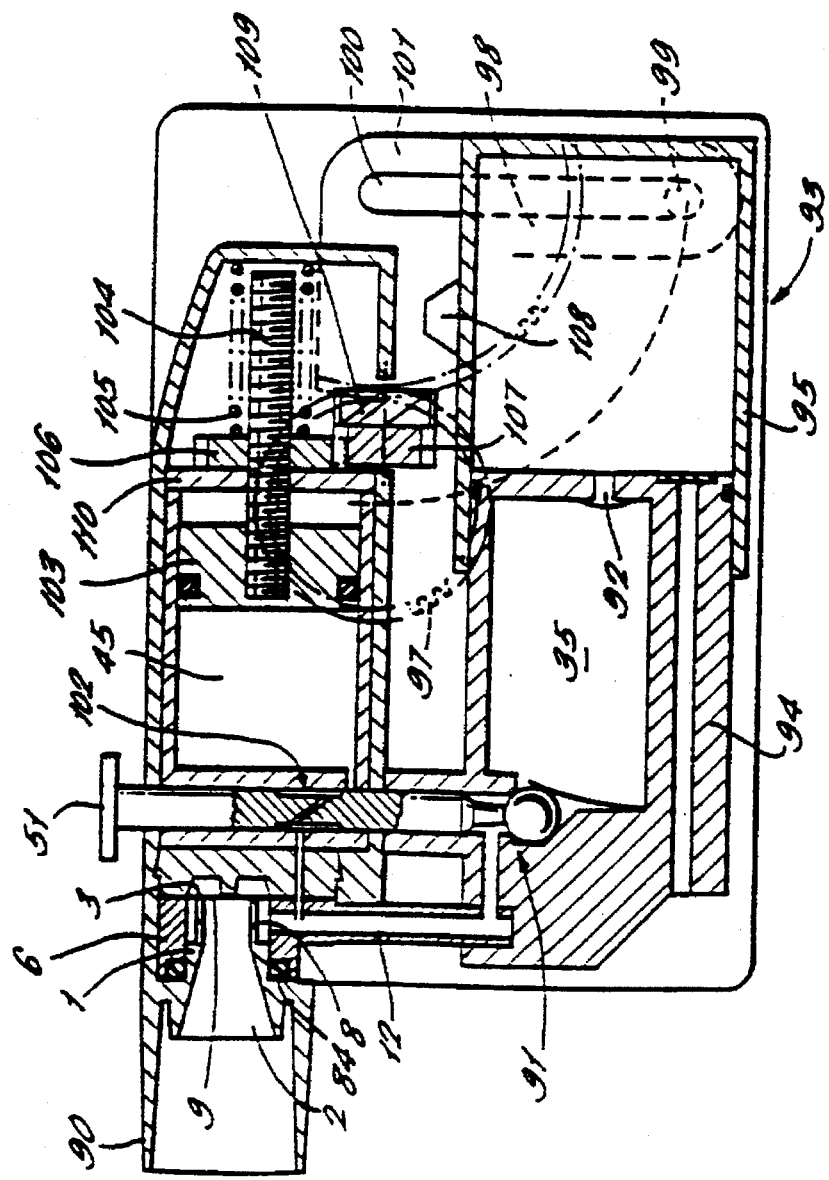

ATOMIZING DISPENSER

This invention relates to a method of dispensing a flowable material in which a quantity of the material is entrained in a flow of gas and is atomised.

Figure 12:
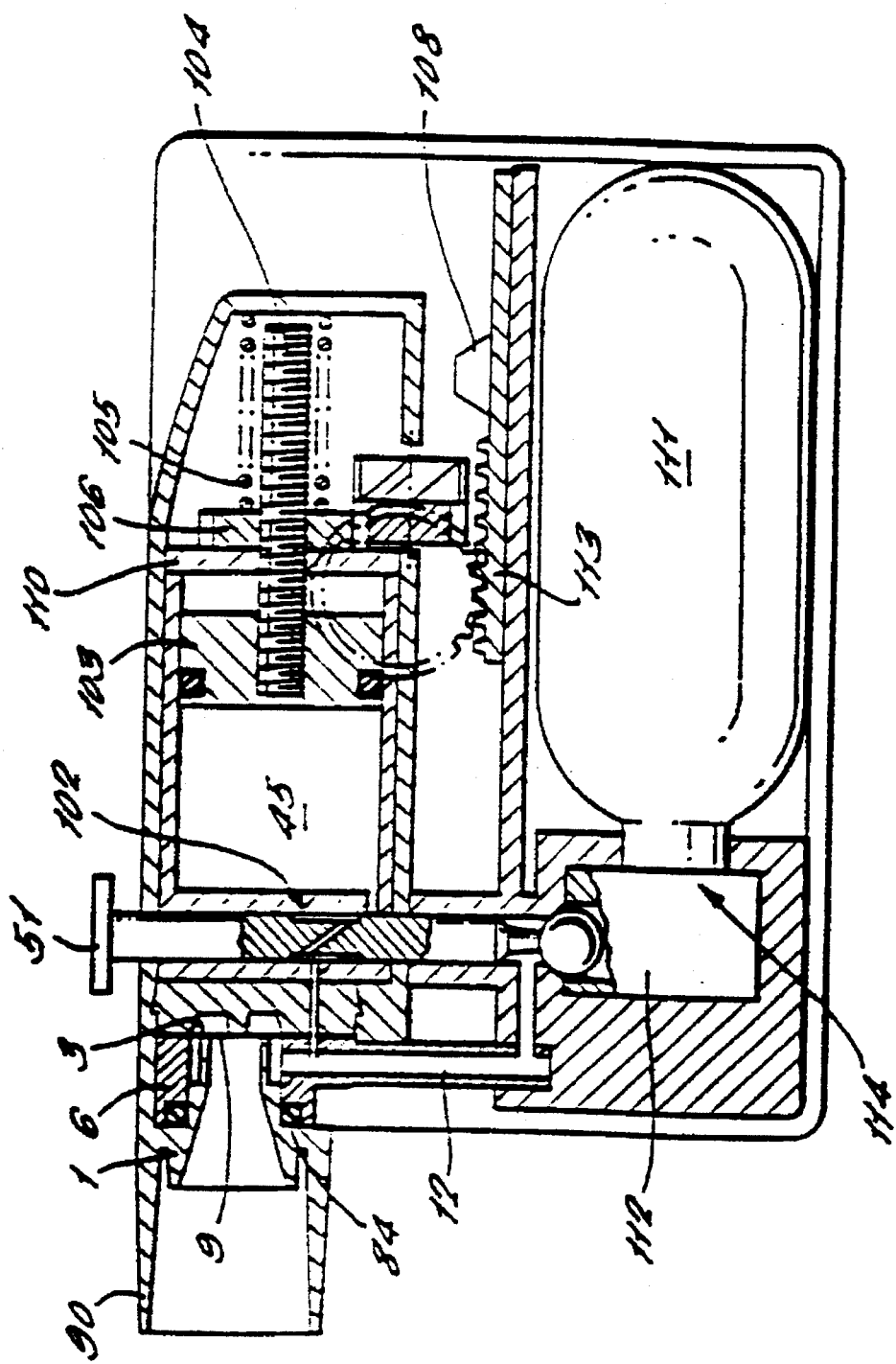

A particular use for such atomisation is in the dispensing of medicinal products where liquid or particulate material should preferably be finely atomised prior to inhalation, it being a known characteristic of inhalation therapy that its effectiveness is critically dependent upon the material being finely atomised in a controlled manner.

Other applications in which atomisation is important include the atomisation of fuel in fuel burners and internal combustion engines and the atomisation of water in humidifiers.

It is an object of the present invention to provide an improved method and apparatus for atomising liquids and particulate solids which provides atomisation in a controlled repeatable fashion together with entrainment of the atomised material in a flow of gas for delivery to a required site.

According to the present invention there is disclosed a method of dispensing a flowable material comprising the steps of supplying pressurised gas to a nozzle such that a flow of gas is discharged through an aperture defined between a lip of the nozzle and a diaphragm, introducing the material into the flow of gas such that material is entrained in the flow, and vibrating the diaphragm so as to atomise the material.

It has been observed that the effect of the vibrating diaphragm on the dispensed material is that atomisation is enhanced. In the case of liquid droplets, a fine mist can be produced in a repeatable fashion and by adjusting the dynamic characteristics of the diaphragm the distribution of droplet size can be tailored to meet specific user requirements in a variety of applications.

Preferably the diaphragm constitutes a wall of a chamber communicating with the aperture, the diaphragm being deformable in response to excess gas pressure in the chamber from a rest position to a displaced position in which the aperture is open to receive the flow passing between the lip and the diaphragm, the method comprising the steps of supplying compressed gas to the chamber such that the diaphragm is deformed into the displaced position and peripherally clamping the diaphragm such that it is maintained under tension in the displaced position whereby the diaphragm is vibrated by the flow of gas.

An advantage of this arrangement is that vibration of the diaphragm is excited and energised by the flow of gas without requiring any additional energy source to provide atomising vibration.

Preferably the diaphragm has an outer portion which defines said wall of the chamber, the lip of the nozzle being annular thereby defining a mouth of an outlet defined by the nozzle and which is traversed by a central portion of the diaphragm in the rest position, and wherein the method includes the step of biasing the diaphragm into contact with the lip when the diaphragm is in its rest position.

It has been observed that positively biassing the diaphragm and lip into contact with one another provides improved performance compared with arrangements in which either the lip remains spaced from the diaphragm in the rest position or in which the lip merely rests in contact with the diaphragm.

Preferably the method includes the step of applying a tensioning force to the diaphragm such that it is maintained under tension in both the rest position and the displaced position.

It is particularly advantageous that the diaphragm should be held in tension in this way if the contact with the lip is minimal or non-existent.

Conveniently ambient air may be admitted to the outlet via an opening defined in the central portion of the diaphragm.

This provides the advantage that ambient air may be drawn through the nozzle to be mixed with the discharged gas, a particular advantage when delivering material for inhalation therapy. A further advantage is that it avoids the formation of a resonant cavity between the diaphragm and housing which would result in damping of the vibration.

The vibrational characteristics of the diaphragm may be modified by the addition of a mass connected to the diaphragm.

This enables the resonant frequency and damping of the diaphragm to be controlled.

The supply of gas may be provided by an air pump providing compressed air to an accumulating reservoir to be subsequently released by action of a trigger.

Alternatively a pressurised container containing pressurised gas may be connected via a metering valve to the chamber for the release of a pulse of gas in response to actuation of the trigger.

For applications such as humidifiers and fuel atomisation, a continuously operating supply of gas may be connected to the chamber.

According to a further aspect of the present invention there is disclosed apparatus for dispensing a flowable material comprising a gas supply for supplying pressurised gas to a nozzle such that a flow of gas is discharged in use through an aperture defined between a lip of the nozzle and a vibratable diaphragm, and dispensing means for introducing a quantity of the material into the flow whereby in use the material is entrained in the flow and atomised by the diaphragm.

Material in the form of a liquid may be dispensed by means of a displacement pump operable to dispense a metered volume of liquid.

Conveniently the dispensing means comprises a cylinder for receiving a quantity of liquid to be dispensed, a piston slidable in the cylinder to dispense liquid therefrom and an indexing mechanism operable to facilitate movement of the piston through predetermined incremental displacements at respective actuations of a trigger mechanism for the gas supply.

Preferred embodiments of the present invention will now be described by way of example only and with reference to the accompanying drawings of which FIG. 1 is a perspective part sectioned view of a nozzle in accordance with the present invention, FIG. 2 is a perspective view of a dispensing apparatus incorporating the nozzle of FIG. 1, FIG. 3 is a schematic diagram showing the operation of the apparatus of FIG. 2, FIG. 4 is a schematic diagram of an alternative apparatus, FIG. 5 is a perpective view of an alternative apparatus, FIG. 6 is a graphical representation of diaphragm displacment as a function of time in response to the release of a pulse of compressed gas through the aperture, FIG. 7 is a sectioned elevation of a diaphragm to which a quantity of particulate material has been added downstream of an annular aperture, FIG. 8 is a sectioned elevation of the nozzle and diaphragm schematically showing movement of the diaphragm to open the aperture, FIG. 9 is a sectioned elevation of an alternative arrangement in which the diaphragm is tensioned by a tensioning ring, FIG. 10 is a sectioned side elevation of a further alternative apparatus incorporating a circular diaphragm of the type shown generally with reference to FIG. 1 and including a hand actuated compressor device for providing compressed air, FIG. 11 is a schematic front view of the apparatus of FIG. 10, and FIG. 12 is a sectioned side elevation of a further alternative apparatus incorporating a pressurised dispensing container.

In FIG. 1 a nozzle 1 defines an outlet 2 which is conically divergent in a direction of flow indicated by arrow A. The nozzle 1 terminates in an annular lip 3 defining a circular mouth 4 of the outlet 2. The nozzle 1 has a cylindrical outer surface 5 which is received in an annular housing 6, the surface 5 having a recessed portion 7 adjacent the lip 3 such that an annular chamber 8 is defined between the housing 6 and the recessed portion 7.

A diaphragm 9 is clamped between the housing 6 and an annular clamp portion 10 and in its relaxed state as shown in FIG. 1 traverses the mouth 4 in contact with the lip 3. In this rest position an outer portion 11 of the diaphragm constitutes an annular wall of the chamber 8. In this closed position the chamber 8 is isolated from the outlet 2.

A gas inlet duct 12 extends radially through the housing 6 into communication with the chamber 8 and similarly a separate liquid inlet duct 13 communicates with the chamber 8 at a location circumferentially spaced from the gas inlet duct 12.

Figure 2:
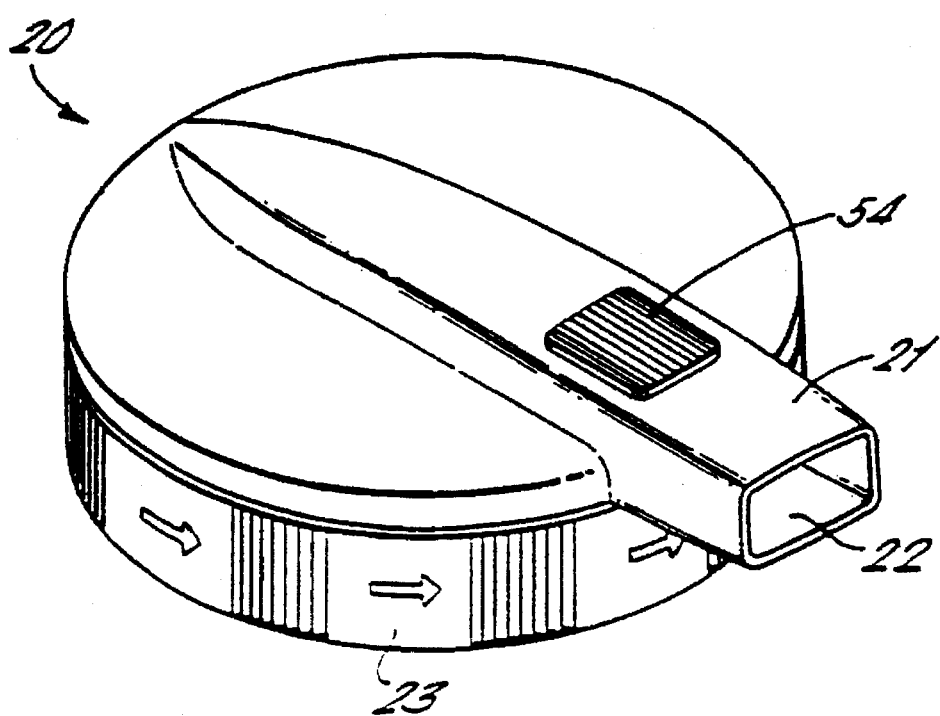

FIG. 2 shows the external appearance of a dispensing apparatus 20 incorporating the nozzle 1 within a mouth piece 21 defining an airway 22 through which in use a user inhales. The apparatus 20 is also provided with an air inlet opening (not shown) allowing air to be drawn into the airway 22 in a manner such that gas emerging from the nozzle 1 will be entrained in the inhaled air flow during inhalation.

Figure 3:
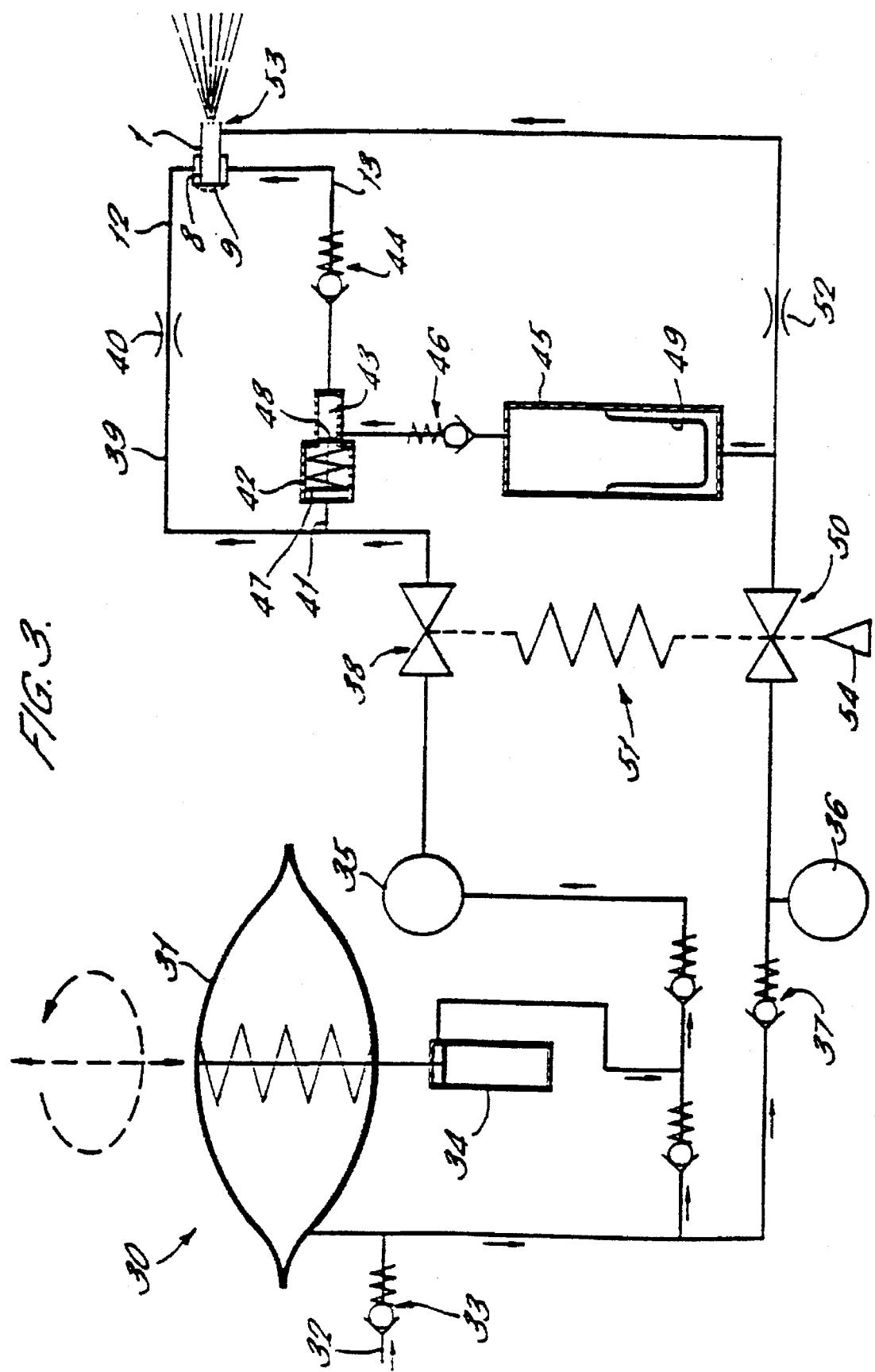
Figure 4:
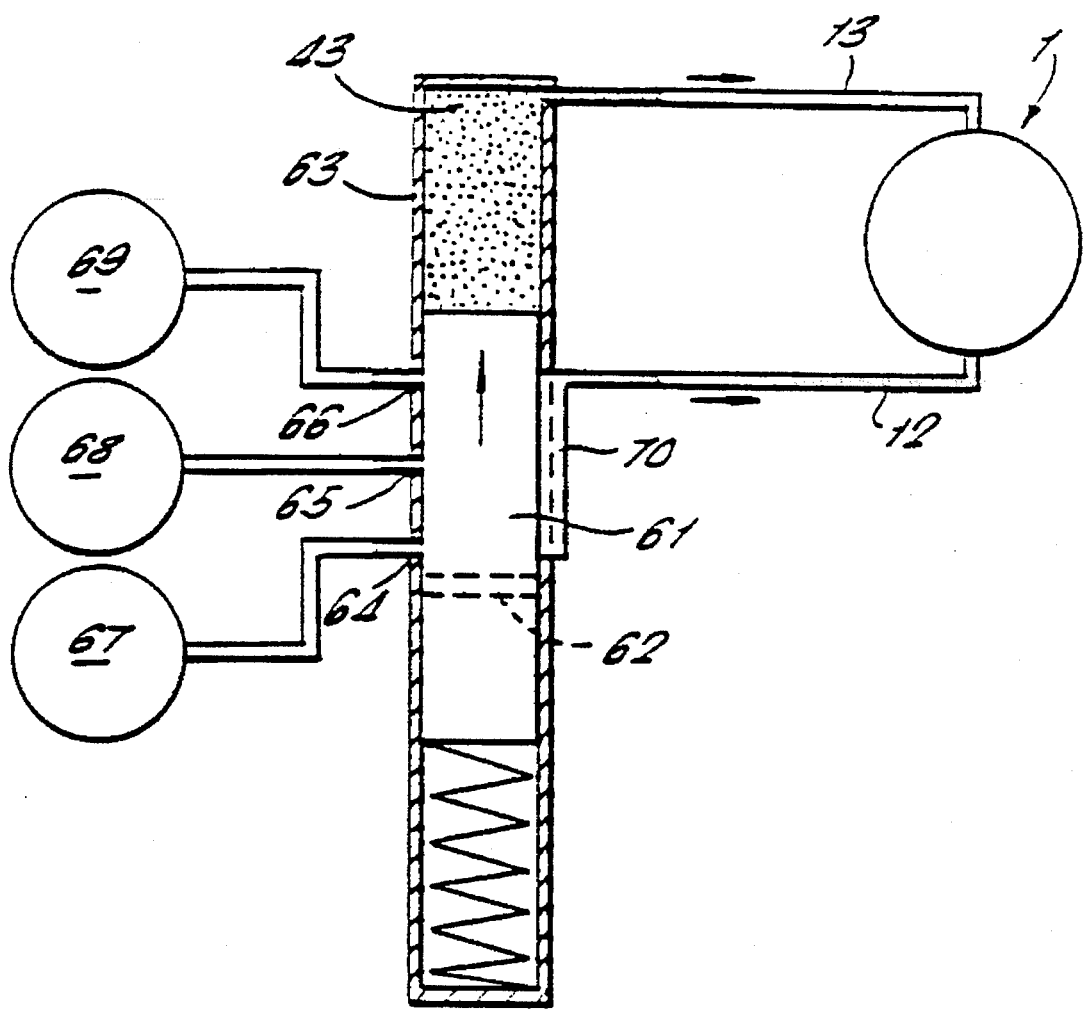
Figure 5:
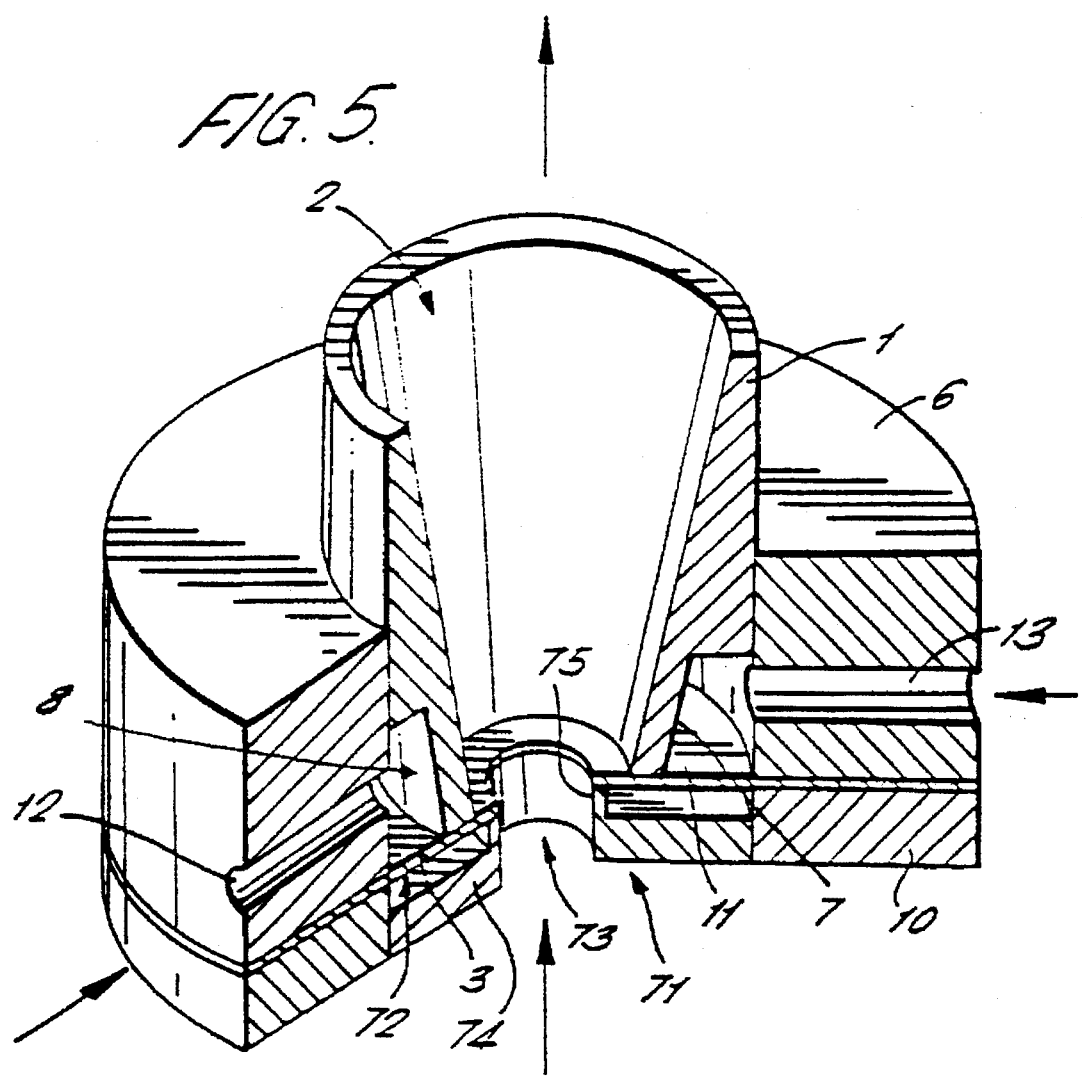

The internal working components of the apparatus 20 are illustrated schematically in FIG. 3 which shows a diaphragm pump 30 of a type which is operated by cam action deriving axial reciprocation of a pump diaphragm 31 from manual rotation of a pump actuator 23 as indicated in FIG. 2.

The pump 30 is connected to an air intake 32 via a one way valve 33 and delivers at each cycle of actuation a low pressure impulse of compressed air to a secondary compressor 34. The secondary compressor 34 is operated by movement of the actuator 23 180° out of phase with the diaphragm pump 30 so as to provide a pressure boosted impulse of compressed air to a high pressure reservoir 35 which when charged contains air at about 5 bar.

The diaphragm pump 30 is also connected to a low pressure reservoir 36 via one way valve 37, air pressure of about 1.5 bar being held in the low pressure reservoir 36 when charged.

The diaphragm pump 30 includes a moulded face cam (not shown) which achieves during a single rotation of the actuator 23 a sequence of 4 axial cycles of the diaphragm to achieve the respective charged pressures referred to above.

The high pressure reservoir 35 is connected via a first valve 38 to a passageway 39 communicating with the chamber 8. The passageway 39 includes a flow restrictor 40 and communicates with a branch passageway 41 to which it is connected upstream of the flow restrictor. The branch passageway 41 communicates with a displacement pump 42 which is arranged to displace a metered volume of liquid from a metering chamber 43 in response to pressurised gas being received through the branch passageway.

The liquid inlet duct 13 communicates with the metering chamber 43 via a one way valve 44 and the metering chamber 43 is supplied with liquid from a liquid reservoir 45 via a further one way valve 46.

The displacement pump 42 has a first piston 47 which is moveable in response to pressurised gas received through the branch passageway 41 to move a second piston 48 arranged to expel liquid from the metering chamber 43. The first and second pistons 47 and 48 are spring loaded into a return position such that return travel of the second piston draws liquid into the metering chamber from the liquid reservoir 45.

The liquid reservoir 45 is partitioned by a flexible bag 49 containing the liquid to be dispensed.

A second valve 50 is operatively connected to the first valve 38 by a trigger mechanism 51. Compressed air is supplied via the second valve 50 from the low pressure reservoir 36 to the liquid reservoir 45 so as to externally pressurise the flexible bag 49. The liquid contents are thereby pressurised and this aids the transfer of liquid into the metering chamber 43.

The output of the second valve 50 is also connected by a further flow restrictor 52 to the outlet 2 of nozzle 1 via a low pressure air port 53 (not shown in FIG. 1).

A trigger 54 is provided as part of the trigger mechanism 51 for operating the first and second valves 38 and 50 and is located on the apparatus 20 adjacent the mouth piece 21 as shown in FIG. 2.

The trigger mechanism 51 is arranged to incorporate a spring mechanism operable such that actuation of the trigger 54 releases the second valve 50 and subsequently releases the first valve 38 thereby ensuring that the metering chamber 43 is filled with liquid and the pistons 47 and 48 are primed prior to release of the first valve 38.

In use, the user manually rotates the actuator 23 through 360° thereby achieving pressurisation of both the high pressure reservoir 35 and the low pressure reservoir 36, this pressurisation being achieved as described above by a multi stage sequence in which the pump diaphragm 31 and secondary compressor 34 are repeatedly cycled.

The user presents the mouth piece 21 ready for inhalation through the airway 22 and manually depresses the trigger 54. The second valve 50 opens thereby externally pressurising the flexible bag 49 and charging the metering chamber 43 with liquid. The first valve 38 then opens and high pressure air delivered via the branch passageway 41 actuates the displacement pump 42 to deliver a metered dose of liquid into the chamber 8.

At the same time high pressured air is transmitted via the flow restrictor 40 to the gas inlet duct 12 and into the chamber 8.

Figure 8:
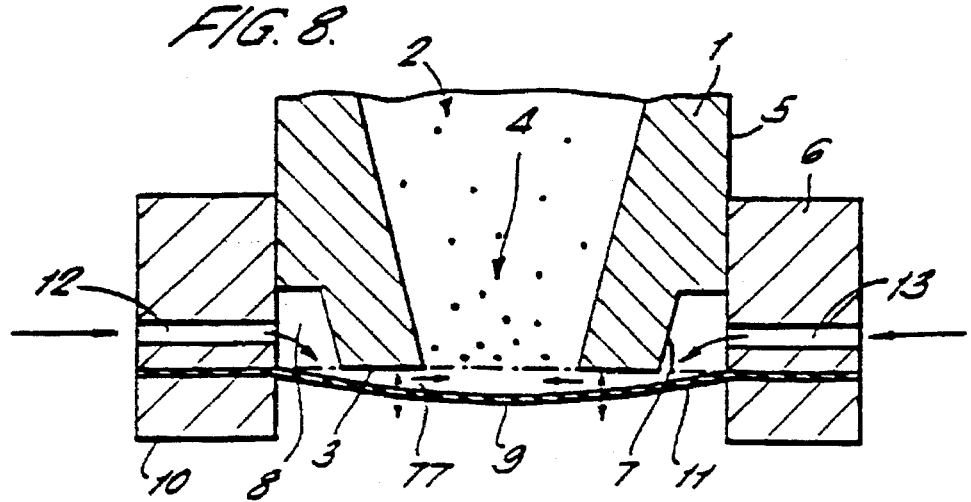

Excess pressure within the chamber 8 acting on the outer portion 11 of the diaphragm 9 unseats the diaphragm from the lip 3 of the nozzle 1 and both compressed air and liquid are ejected from the chamber 8 via an aperture 77 defined between the lip and the diaphragm into the outlet 2 as shown in FIG. 8.

Figure 6:
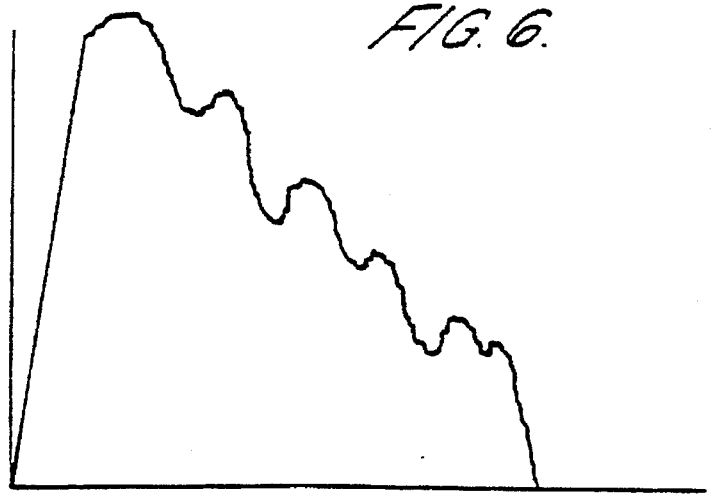
Figure 7:
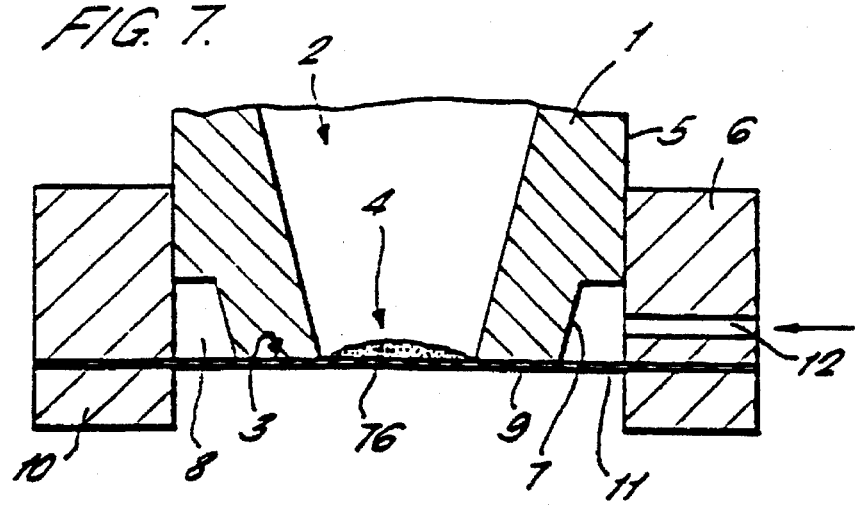

FIG. 6 illustrates graphically the displacement of the diaphragm 9 away from the lip 3 as a function of time in response to a pulsed flow of gas being delivered to the chamber 8. The diaphragm 9 initially moves rapidly to its fully displaced position in response to an impulse of gas received within the chamber 8, the displacement of the diaphragm then progressively relaxing with decreasing gas pressure towards its rest position in which the aperture reduces to zero. A high frequency vibration of the diaphragm is superimposed on this displacement, the vibration being excited and energised by the flow of gas in a similar manner to that which is achieved in a conventional air horn such as those used in motor vehicles.

Liquid entrained in the flow of gas has been observed to exit the aperture between the lip 3 and the diaphragm 9 as a wall jet with an initial velocity which is directed radially inwardly, the jet then forming extended ligaments which break up into droplets.

The effect of the vibration present in the diaphragm 9 has been observed to be a marked reduction in the size of the droplets which are ultimately entrained in the air exiting from the outlet 2. The precise mechanism by which the vibration of the diaphragm 9 achieves this enhanced atomisation is believed to involve impact between the diaphragm and droplets and the effects of air currents created by the movement of the diaphragm.

A finely atomised mist of liquid is thereby produced in the airway 22 and is inhaled via the mouth piece 21. The flow velocity of the inhaled air is boosted by a secondary flow of air received via low pressure air port 53. The oscillation of the diaphragm continues until the available air pressure is no longer sufficient to unseat the diaphragm, the time constant of the oscillation being much smaller than the time taken for the gas pressure to fully depleat.

In a prototype of the nozzle arrangement shown in FIG. 1, a diaphragm having an exposed face of 8.5 mm diameter and cooperating with a lip of 6 mm diameter was found to operate satisfactorily when energised with an impulse of compressed air from a reservoir of 10 cc volume with an initial pressure of 5 bar. The diaphragm was found to oscillate at frequencies extending through the audible and into the ultrasonic range.

The duration of the air impulse was of the order of 1 second. It was found that a liquid could be atomised in such an arrangement such that 90% of droplets were of less than 20 microns diameter, 60% were less than 10 microns diameter and 30% below 5 microns.

Satisfactory redispersion of powders having single particle size of 3 microns was also achieved, the single particles being initially coalesced into larger granules and atomised during the dispensing operation. Dispensing such powders was achieved by orienting the nozzle 1 such that the outlet 2 extended upwardly from the diaphragm 9, particles of solid material being inserted into the outlet so as to initially rest on the diaphragm. The material in this situation was therefore introduced downstream of the aperture subsequently defined between the lip 3 and the diaphragm 9 in response to the gas flow. Dispersion of the particulate solid material in this arrangement is believed to be primarily as a result of impact between the diaphragm and the material, the material then being dispersed into a fine powder which becomes entrained in the gas flow. Droplets of liquid may similarly be dispersed and atomised by introducing the liquid so as to rest upon the diaphragm.

It should be noted that the illustration in FIG. 8 of the opening of the aperture 77 is schematic and that in practice a complex mode of vibration set up in the diaphragm will result in the instantaneous cross section of the diaphragm having multiple peaks.

A modified arrangement is illustrated in FIG. 4 which will now be described using corresponding reference numerals to those of preceding Figures where appropriate for corresponding features.

The modified apparatus of FIG. 4 has a nozzle 1 of the type shown in FIG. 1 receiving compressed air via a gas inlet duct 12 and a supply of liquid via a liquid inlet duct 13.

A metering chamber 43 containing liquid receives a cylindrical piston 61 operable to displace the liquid and which includes a diametrically extending bore 62 allowing the piston 61 to also act as a shuttle valve for the release of compressed air. The piston 61 is slidable in a cylinder 63 having axially spaced air inlet ports 64, 65 and 66 connected to respective first, second and third high pressure air reservoirs 67, 68 and 69. Movement of the piston 61 along the cylinder 63 brings the bore 62 sequentially into registration with the first, second and third air inlet ports 64, 65 and 66 thereby constituting a valve means 61, 62, 63 allowing the compressed air to be conducted via an outlet port 70 into the gas inlet duct 12.

The valve means 61, 62, 63 may be incorporated into the apparatus of preceding Figures in order to deliver sequentially three separate impulses of compressed air during the discharge of liquid from the chamber 43. This modification takes account of the tendency for the liquid discharge to take longer to complete than the duration of an impulse of compressed air released from the high pressure reservoir.

In FIG. 5 the nozzle 1 of FIG. 1 is provided with an alternative diaphragm assembly 71 and will now be described using corresponding references to those of FIG. 1 where appropriate for corresponding elements.

The arrangement of FIG. 5 consists of a nozzle 1 defining an outlet 2 and an annular lip 3 defining a circular mouth 4 of the outlet.

The nozzle 1 is received in an annular housing 6 and an annular chamber 8 is defined between the housing and a recessed portion 7 of the outer surface 5 of the nozzle 1.

The diaphragm assembly 71 comprises a modified diaphragm 72 having a central opening 73 through which ambiant air may be drawn so as to flow through the outlet 2.

The diameter of the opening 73 is less than that of the internal diameter of the lip 3 so that the presence of the opening does not affect the operational relationship between the lip and the diaphragm 72.

A disc 74 is slidably received within the housing 6 immediately upstream of the diaphragm 72 and includes an axially projecting cylindrical projection 75 which is bonded to the diaphragm 72 peripherally of the opening 73.

The cylindrical projection 75 has an internal diameter equal to that of the opening 73 so that inhaled air may pass through the disc 74.

The disc 74 has the effect of adding a localised mass to the diaphragm 72 adjacent to its point of maximum vibrational movement and the effect of this additional mass is to modify the vibrational characteristics of the diaphragm and in particular has been found to be effective in reducing unwanted noise.

In an alternative arrangement (not shown) a disc may be added to the diaphragm without the presence of an opening 73 in order to modify its noise characteristics but without providing additional air flow through the diaphragm.

A further alternative is to provide the diaphragm 72 with an opening 73 but to not include disc 74 thereby providing additional air flow but without modifying the vibrational characteristics of the diaphragm.

In the above described arrangements the diaphragm 9 is peripherally clamped by a clamp portion 10 such that deformation of the diaphragm in response to the flow of gas to thereby define the aperture 77 results in the diaphragm being maintained under tension. The existence of this tension enables the vibration in the diaphragm to be sustained. It has been observed that the characteristics of vibration may be modified by varying the tension and to this end the diaphragm may be pre-loaded by means of a tensioning device 80 as illustrated in FIG. 9 which will now be described using corresponding reference numerals to those of preceding Figures where appropriate for corresponding elements.

The tensioning device 80 comprises a tensioning ring 81 which is moved into contact with the diaphragm after the diaphragm has been clamped thereby deforming and tensioning the diaphragm in its rest position. The tensioning ring 81 is held by a screw adjustor 82 which is movable by a screw thread mechanism relative to the housing 6 to axially displace the tubular tensioning ring 81 relative to the clamp portion 10, thereby achieving a controlled amount of deformation of the diaphragm and thereby controlling tension.

Since this adjustment of the tensioning ring 81 axially displaces the location of the diaphragm within the housing 6, corresponding adjustment of the position of the lip 3 is desirable and in this example is facilitated by a screw threaded adjusting mechanism 83 whereby the nozzle 1 is axially adjustable relative to the housing 6 by rotating the nozzle to achieve axial adjustment.

An O-ring seal 84 is provided between the nozzle 1 and housing 6 to prevent the escape of gas from the chamber 8.

By adjusting the tension in the diaphragm 9 the vibrational characteristic and hence the atomising properties of the diaphragm 9 have been found to be adjustable so that the droplet size distribution present in the outlet 2 can be tailored to meet the requirements of particular products or uses of the device.

In the preferred embodiments described above the lip 3 is shown to contact the diaphragm 9 in the rest position of the diaphragm. This need not necessarily be the case since a small gap between the diaphragm and the lip in the rest position still provides a working arrangement, the diaphragm being vibratable provided that it is maintained under tension. The best results however have been obtained by maintaining the lip 3 in contact with the diaphragm in the rest position and adjusting the axial location at which the diaphragm is peripherally clamped such that a positive bias is exerted on the lip by the diaphragm, the bias being derived from tension established within the diaphragm.

In FIGS. 10 and 11 a further alternative apparatus is illustrated and is of a type which incorporates a circular diaphragm in a configuration which may be as shown in FIGS. 1, 5, 7, 8 or 9.

The apparatus of FIG. 11 incorporates a nozzle 1 which is axially extended to form a mouth piece 90 suitable for oral inhalation. A circular diaphragm 9 is clamped in contact with a lip 3 of the nozzle 1 and is deformable to define an aperture communicating between a nozzle outlet 2 and an annular chamber 8 defined between the housing and the nozzle.

An inlet duct 12 communicates with the chamber 8 and is arranged to receive a flow of compressed air from a valve 91 actuated by depression of a trigger 51.

The valve 91 is arranged to release compressed air held within a reservoir 35 which receives air via a one way valve 92 from a displacement pump 93 which comprises a fixed piston 94 and a movable cylinder 95.

The pump 93 is actuated by manual rotation of a circular handle 96 as shown in FIG. 11 which is connected to a first gear wheel 97 engaged to a geared quadrant 98 such that the quadrant 98 is rotated through 90° by corresponding rotation of the handle 96.

Rotation of the quadrant 98 is translated to linear reciprocating motion of the cylinder 95 by means of a cam follower 99 mounted on the quadrant and received in a linear cam slot 100 formed in a plate 101 connected to the cylinder.

The trigger 51 is also arranged to release a metered dose of liquid from a liquid reservoir via a spool valve arrangement 102 allowing liquid to pass from the reservoir 45 into the inlet duct 12 when the trigger is depressed.

Liquid in the liquid reservoir 45 is pressurised by action of a piston 103 mounted on a lead screw 104 which is spring loaded by operation of a spring 105.

At each actuation of the trigger 51 the lead screw is allowed to move forward by an indexed amount determined by a priming operation effected by rotation of a drive gear 106 which is threadedly engaged on the lead screw 104 such that relative rotational movement between the drive gear 106 and the lead screw 104 is accompanied by relative axial displacement.

The drive gear 106 is peripherally engaged by an indexing gear 107 mounted on an axis parallel to the lead screw 104 and arranged such that rotation of the indexing gear through a predetermined angle results in rotation of the driven gear by an extent determining the required axial displacement of the lead screw to achieve the metered dose.

The indexing gear 107 is rotated by action of a detent 108 mounted on the cylinder 95 and engaging a coarse helical gear portion of the indexing gear such that at each axial reciprocation of the cylinder the indexing gear is caused to rotate through a predetermined angle.

In use the handle 96 is rotated so as to correspondingly turn the quadrant 98 through 90°. This causes the cylinder to reciprocate relative to the fixed piston 94 thereby injecting compressed air into the reservoir 35 and at the same time resulting in rotation of the indexing gear 107 through a predetermined angle.

The drive gear 106 is correspondingly rotated and caused to move axially relative to the lead screw 104 in a direction away from an end stop 110 towards which it is biassed by action of the spring 105. During this priming operation the lead screw 104 is held stationary since the piston 104 cannot move while the spool valve 102 remains closed, the liquid within reservoir 45 being incompressable.

A user presents the mouth piece 90 to his mouth ready for inhalation and then depresses the trigger 51. The valve 91 is thereby opened to release compressed air from reservoir 35 through the inlet duct 12 to the chamber 8, the compressed air thereby acting on the diaphragm 9 to open an aperture between the diaphragm and the lip 3 and establish a discharge of air accompanied by vibration of the diaphragm.

At the same time the spool valve 102 releases liquid from the liquid reservoir 45 to be mixed with the flow of air within the inlet duct 12, liquid then being entrained in the discahrged air passing through the aperture. A wall jet of liquid under pressure emerges from the aperture between the lip 3 and the diaphragm 9 and travels generally parallel to the diaphragm, thereby being atomised by surface tension effects and by interaction with the vibrating diaphragm before being entrained in the flow of air passing out of the outlet into the mouth piece 90 for inhalation.

The discharge of liquid from the reservoir 45 is accompanied by an incremental movement of the piston 103, the travel of the piston being interrupted by engagement between the drive gear 106 and the end stop 110.

The trigger 51 is then returned to its initial position and the apparatus is again ready for use.

A further alternative apparatus is shown in FIG. 12 which is based on the apparatus of Figures 10 and 12 but not including a piston and cylinder arrangement for compressing air. Instead, a pressurised container 111 charged with compressed gas is connected via a releasable connector 114 to a metering valve 112, the metering valve being operable by depression of the trigger 51 to discharge into the inlet duct 12 a metered pulse of compressed gas. The releasable connector 114 allows replacement containers to be fitted to replenish the supply of gas. Typically the compressed gas is carbon dioxide.

The apparatus is primed by rotation of handle 96 resulting in linear reciprocation of detent 108 via a linear rack 113 to index the drive gear 106 in readiness for dispensing a metered dose of liquid from liquid reservoir 45.

Operation of the apparatus of FIG. 12 is otherwise similar to the operation of the apparatus of FIGS. 10 and 11 in that depression of the trigger 51 causes the release of both compressed gas and liquid into the inlet duct 12 to be dispensed via nozzle 1 into the mouth piece 90.

Further alternatives and modifications to the above apparatus and method are envisaged including an alternative arrangement in which liquid or powder is injected into the nozzle outlet by a dispensing means at a location downstream of the diaphragm.

Alternatively powder may be injected into the chamber 8 by a suitable mechanism, the powder being initially injected in either a single mass of coalesced particles or relatively coarse granules, the effect of being injected through the nozzle and subjected to the passage of the flow across the vibrating diaphragm being to micronise the powder.

The additional provision of a low pressure air flow to boost the rate of delivery of the atomised liquid or powder may be provided by injecting the secondary air flow into an annular space surrounding the nozzle. This secondary air flow may not be essential and it is envisaged that this step could be omitted from the above apparatus and method.

Apparatus intended for inhalation therapy may be provided with a breath actuated trigger in place of a manual actuator or may alternatively be provided with an automatically functioning trigger such as an electrical timer.

The apparatus may be provided as a disposable item or may include a re-usable portion into which a disposable reservoir of the material can be inserted.

The invention may be utilised in atomising material other than for inhalation therapy in which case an air duct other than a mouth piece would be provided.

Alternative mechanisms for metering the material may be employed such as conventional liquid metering pump arrangements.

The apparatus is conveniently moulded from plastics materials and the diaphragm may be a film comprising metal foil, polyester film, kapton film, or a laminate. Selection of the material will depend upon comparability with the material to be dispensed but in any event should be selected to be dimensionally stable and tear resistant.

The apparatus may be provided with an air control valve in order to adjust the speed of air discharged from the air reservoir to the nozzle.

The apparatus may be modified to provide for a purging impulse of air or gas to be delivered in a separate actuation following an actuation to deliver atomised material. The accumulation of residues in the apparatus may whereby be avoided. This is particularly useful when dispensing water based liquid products and especially those containing solids in suspension.

In the preferred embodiments described with reference to FIGS. 1 to 12 refer to a single air inlet duct communicating with an annular chamber 8. It has in fact been found to be advantageous to provide a plurality of gas inlet ducts communicating with the chamber at circumferentially spaced locations in order to ensure that the gas pressure is applied evenly to the diaphragm. This has the advantage of avoiding the appearance of vortices in the flow within the outlet, the formation of such vortices being found to be detrimental to the atomisation process.

The apparatus described above with reference to FIGS. 1, 5, 8, 9 and 11 may alternatively be utilised with a continuously operating supply of pressurised gas for use in such applications as fuel atomisation and humidifiers.

We claim:

1. A method of dispensing a flowable material comprising the steps of:

introducing the material into a flow of gas such that the material is entrained in the flow of gas, supplying pressurised gas to a nozzle such that the flow of pressurised gas is discharged through an aperture defined between a lip of the nozzle and a diaphragm, such that the flow of pressurised gas has an initial direction which is radially inward, and vibrating said diaphragm so as to atomise the material;

said diaphragm constituting a wall of a chamber which is in communication with said aperture, said diaphragm being deformable from a rest position in response to excess gas pressure in said chamber to a displaced position whereby said aperture is opened to receive the flow of pressurised gas passing between said lip and said diaphragm, the pressurised gas being supplied via said chamber such that said diaphragm is deformed into the displaced position, said diaphragm being peripherally clamped about said nozzle such that said diaphragm is maintained under tension in the displaced position, whereby said diaphragm is vibrated by the flow of pressurised gas, said diaphragm having an outer portion which defines said wall of said chamber, said lip of the nozzle defining a mouth of an outlet defined by the nozzle, said mouth traversed and closed by a central portion of said diaphragm in the rest position.

2. A method as claimed in claim 1 including the step of applying a tensioning force to said diaphragm such that said diaphragm is maintained under tension in both the rest position and the displaced position.

3. A method of dispensing a flowable material comprising the steps of introducing the material into a flow of gas such that material is entrained in the flow of gas, supplying pressurised gas to a nozzle such that the flow of gas is discharged through an aperture defined between a lip of the nozzle and a diaphragm, vibrating said diaphragm so as to atomise the material, and admitting ambient air to an outlet via an opening defined in a central portion of said diaphragm;

said diaphragm constituting a wall of a chamber which is in communication with said aperture said diaphragm being deformable from a rest position in response to excess gas pressure in said chamber to a displaced position in which said aperture is opened to receive the flow of gas passing between said lip and said diaphragm, the pressurised gas being supplied via said chamber such that said diaphragm is deformed into the displaced position and said diaphragm being peripherally clamped such that said diaphragm is maintained under tension in the displaced position whereby said diaphragm is vibrated by the flow of gas, said diaphragm having an outer portion which defines said wall of said chamber, said lip of the nozzle defining a mouth of the outlet defined by the nozzle, said mouth traversed by a portion of the diaphragm in the rest position.

4. A method as claimed in claim 3 including the step of modifying the vibrational characteristics of the diaphragm by a mass connected to said diaphragm.

5. A method as claimed in claim 3 wherein the gas supply includes an air pump;

the method further including the steps of operating the air pump to accumulate a volume of compressed air and operating a trigger to release the compressed air through a passageway connected to the chamber.

6. A method as claimed in claim 5 including the steps of containing the accumulated volume of compressed air in a plurality of reservoirs and releasing the compressed air from the reservoirs to thereby extend the duration of the flow of gas.

7. A method of dispersing a flowable material comprising the steps of introducing the material into a flow of gas such that material is entrained in the flow of gas, supplying pressurised gas to a nozzle such that the flow of gas is discharged through an aperture defined between a lip of the nozzle and a diaphragm, vibrating said diaphragm so as to atomise the material, and discharging a secondary flow of gas through an outlet such that the secondary flow of gas is introduced into the flow of gas at a location downstream of said aperture with respect to the direction of flow; and said diaphragm constituting a wall of a chamber which is in communication with said aperture said diaphragm being deformable from a rest position in response to excess gas pressure in said chamber to a displaced position in which said aperture is opened to receive the flow of gas passing between said lip and said diaphragm, the pressurised gas being supplied via said chamber such that said diaphragm is deformed into the displaced position and said diaphragm being peripherally clamped such that said diaphragm is maintained under tension in the displaced position whereby said diaphragm is vibrated by the flow of gas, said diaphragm having an outer portion which defines said wall of the chamber, said lip of the nozzle defining a mouth of the outlet defined by the nozzle, said mouth traversed by a central portion of the diaphragm in the rest position.

8. A method as claimed in claim 7 including the step deriving the secondary flow of gas from a secondary gas supply at a lower pressure than that of the gas supplied to said chamber.

9. A method as claimed in claim 3 wherein the material is a liquid and includes the step of introducing the liquid into the flow of gas at a location upstream of said aperture with respect to the direction of gas flow.

10. A method as claimed in claim 3 wherein the material is a liquid and includes the step of injecting a measured volume of the liquid into the flow of gas by operation of a displacement pump.

11. A method as claimed in claim 3 includes the step of introducing the material into the outlet at a location downstream of the closable aperture and in contact with said diaphragm.

12. A method as claimed in claim 11 wherein the material is a particulate solid in the form of loose or consolidated powder.

13. Apparatus for dispensing a flowable material comprising:

a nozzle, a gas supply for supplying pressurised gas to said nozzle such that a flow of gas is discharged in use through an aperture defined between a lip of said nozzle and a vibratable diaphragm, such that the flow of gas has an initial direction which is radially inward, a dispensing means for introducing a quantity of the material into the flow of gas whereby in use the material is entrained in the flow of gas prior to the flow of gas entering said aperture and atomised by said diaphragm, a housing defining a chamber connected to the gas supply, and which is in communication with an outlet defined by said nozzle via said aperture, and a clamp means peripherally clamping said diaphragm such that said diaphragm is maintained under tension when deformed into the displaced position whereby said diaphragm is vibratable by the flow of gas;

said diaphragm constituting a wall of said chamber and being deformable in response to excess pressure in said chamber from a rest position to a displaced position in which said aperture is opened;

said diaphragm is peripherally clamped by said clamp means such that an outer portion of said diaphragm defines said wall of said chamber; and said lip to thereby define a mouth of the outlet which is traversed by a central portion of said diaphragm.

14. Apparatus as claimed in claim 13 further comprising tensioning means operable to apply a tensioning force to said diaphragm in the rest position.

15. Apparatus as claimed in claim 13 wherein said diaphragm in its rest position is in contact with and exerts a biassing force on said lip.

16. Apparatus for dispensing a flowable material comprising:

a nozzle, a gas supply for supplying pressurised gas to said nozzle such that a flow of gas is discharged in use through an aperture defined between a lip of said nozzle and a vibratable diaphragm, a dispensing means for introducing a quantity of the material into the flow of gas whereby in use the material is entrained in the flow of gas and atomised by said diaphragm, a housing defining a chamber connected to said gas supply, and said housing is in communication with an outlet defined by said nozzle via said aperture, and a clamp means peripherally clamping said diaphragm such that said diaphragm is maintained under tension when deformed into the displaced position whereby said diaphragm is vibratable by the flow of gas;

said diaphragm constituting a wall of said chamber and being deformable in response to excess pressure in said chamber from a rest position to a displaced position in which said aperture is opened;

said diaphragm is peripherally clamped by said clamp mean such that an outer portion of said diaphragm defines said wall of said chamber;

said lip defines a mouth of the outlet which is traversed by a portion of said diaphragm; and the central portion of said diaphragm defines a central opening communicating between ambient air and the outlet.

17. Apparatus as claimed in claim 16 includes a mass connected to said diaphragm.

18. Apparatus as claimed in claim 16 wherein the gas supply includes an air pump and a reservoir means operable to accumulate a volume of compressed air delivered by said air pump, the apparatus further includes a trigger operable to release the compressed air to flow to said chamber via a passageway defined in said housing.

19. Apparatus as claimed in claim 18 wherein the reservoir means includes a plurality of reservoirs and valve means operable to release the compressed air sequentially therefrom to thereby extend the duration of the flow of gas.

20. Apparatus as claimed in claim 16 wherein said gas supply includes a connector means for releasibly connecting a pressurised gas container in communication with said chamber via a valve operable to release a pulse of compressed gas.

21. Apparatus as claimed in claim 16 wherein said gas supply includes a supply means for continuously supplying pressurised gas to said chamber.

22. Apparatus as claimed in claim 16 includes an inlet duct for introducing the material into the flow of gas, and said inlet duct is in communication with said chamber at a location upstream of the closable aperture with respect to the direction of the flow of gas.

23. Apparatus as claimed in claim 22 for use in dispensing material in the form of liquid wherein said dispensing means includes a displacement pump operable to dispense a metered volume of liquid.

24. Apparatus as claimed in claim 23 wherein the dispensing means includes:
a cylinder for receiving a quantity of liquid to be dispensed,
a piston slidable in the cylinder to displace liquid therefrom, and
an indexing mechanism operable to facilitate movement of said piston through predetermined incremental displacements at respective actuations of a trigger mechanism for said gas supply.

25. Apparatus as claimed in claim 16 includes a secondary discharge means for discharging a secondary flow of gas through the outlet at a location downstream of said aperture with respect to the direction of the flow of gas.

26. Apparatus as claimed in claim 25 wherein the secondary discharge means includes a secondary gas supply operable to supply gas at a lower pressure than that supplied to said chamber.

27. A method of dispensing a flowable material comprising the steps of:
supplying pressurised gas to a nozzle such that a flow of gas is discharged through an aperture defined between a lip of the nozzle and a diaphragm,
introducing the material into the flow of gas such that the material is entrained in the flow,
vibrating said diaphragm so as to atomise the material, wherein said diaphragm constitutes a wall of a chamber communicating with said aperture, and
modifying the vibrational characteristics of said diaphragm by a mass connected to said diaphragm;
said diaphragm being deformable in response to excess gas pressure in said chamber from a rest position to a displaced position in which said aperture is opened to receive the flow of gas passing between said lip and said diaphragm, the pressurised gas being supplied via said chamber such that said diaphragm is deformed into the displaced position and said diaphragm being peripherally clamped such that said diaphragm is maintained under tension in the displaced position whereby said diaphragm is vibrated by the flow of gas.

28. Apparatus for dispensing a flowable material comprising:
a nozzle,
a gas supply for supplying pressurised gas to the nozzle such that a flow of gas is discharged in use through an aperture defined between a lip of the nozzle and a vibratable diaphragm,
a dispensing means for introducing a quantity of the material into the flow of gas whereby in use the material is entrained in the flow of gas and atomised by said diaphragm,
a housing defining a chamber connected to said gas supply and communicating with an outlet defined by said nozzle via said aperture,
a clamp means peripherally clamping said diaphragm such that said diaphragm is maintained under tension when deformed into the displaced position whereby said diaphragm is vibratable by the flow of gas, and
a mass connected to said diaphragm so as to modify its vibrational characteristics; and
said diaphragm constituting a wall of said chamber and being deformable in response to excess pressure in said chamber from a rest position to a displaced position in which said aperture is opened.

29. A method of dispensing a flowable material comprising the steps of:
operating a pump to accumulate a volume of compressed gas,
operating a trigger to release the compressed gas through a passageway connected to a chamber,
supplying pressurised gas from a gas supply including said air pump to a nozzle such that a flow of gas is discharged through an aperture defined between a lip of the nozzle and a diaphragm,
introducing the material into the flow of gas such that the material is entrained in the flow, and
vibrating said diaphragm so as to atomise the material; and
said diaphragm constituting a wall of said chamber communicating with said aperture, said diaphragm being deformable in response to excess gas pressure in said chamber from a rest position to a displaced position in which said aperture is opened to receive the flow of gas passing between said lip and said diaphragm, the pressurised gas being supplied via said chamber such that said diaphragm is deformed into the displaced position and said diaphragm being peripherally clamped such that it is maintained under tension in the displaced position whereby said diaphragm is vibrated by the flow of gas.

30. A method as claimed in claim 29 including the steps of:
containing the accumulated volume of compressed gas in a plurality of reservoirs and
releasing the compressed gas from the reservoirs to thereby extend the duration of the flow of gas.

31. Apparatus for dispensing a flowable material comprising:
a nozzle,
a gas supply for supplying pressurised gas to the nozzle such that a flow of gas is discharged in use through an aperture defined between a lip of said nozzle and a vibratable diaphragm, the gas supply having a pump and a reservoir means operable to accumulate a volume of compressed gas delivered by said pump,
a dispensing means for introducing a quantity of the material into the flow of gas whereby in use the material is entrained in the flow of gas and atomised by said diaphragm, a housing defining a chamber connected to said gas supply and communicating with an outlet defined by said nozzle via said aperture, a clamp means peripherally clamping said diaphragm such that said diaphragm is maintained under tension when deformed into the displaced position whereby said diaphragm is vibratable by the flow of gas, and a trigger operable to release the compressed gas to flow to said chamber via a passageway defined in said housing; and said diaphragm constituting a wall of said chamber and being deformable from a rest position in response to excess pressure in said chamber to a displaced position in which the aperture is opened.

32. Apparatus as claimed in claim 31 wherein the reservoir means includes a plurality of reservoirs and a valve means operable to release the compressed gas sequentially therefrom to thereby extend the duration of the flow of gas.

33. An apparatus as claimed in claim 32 wherein the gas is air.

34. A method as claimed in claim 30 wherein the gas is air.

* * * * *